United States Patent [19]

Lee et al.

[11] Patent Number: 5,723,700
[45] Date of Patent: Mar. 3, 1998

[54] METHOD FOR CONCURRENTLY PRODUCING 1,1,1,2-TETRAFLUOROETHANE AND PENTAFLUOROETHANE

[75] Inventors: Byung Gwon Lee; Hoon Sik Kim; Honggon Kim; Sang Deuk Lee; Moon Jo Chung, all of Seoul, Rep. of Korea

[73] Assignee: Korea Institute of Science and Technology, Seoul, Rep. of Korea

[21] Appl. No.: 708,466

[22] Filed: Sep. 5, 1996

[30] Foreign Application Priority Data

Apr. 23, 1996 [KR] Rep. of Korea ............... 12394/1996

[51] Int. Cl.⁶ .................................................. C07C 17/08
[52] U.S. Cl. ................................... 570/168; 570/169
[58] Field of Search .................................... 570/168, 169

[56] References Cited

U.S. PATENT DOCUMENTS

| | | |
|---|---|---|
| 3,157,707 | 11/1964 | Clark ................................. 570/169 |
| 5,258,561 | 11/1993 | Nappa et al. |
| 5,382,722 | 1/1995 | Scott et al. .......................... 570/168 |
| 5,500,400 | 3/1996 | Kim et al. |

FOREIGN PATENT DOCUMENTS

| | | | |
|---|---|---|---|
| 0513823 | 11/1992 | European Pat. Off. | ............ 570/169 |
| 93/25505 | 12/1993 | WIPO . | |

*Primary Examiner*—Alan Siegel
*Attorney, Agent, or Firm*—Darby & Darby

[57] ABSTRACT

There is a method for concurrently producing 1,1,1,2-tetrafluoroethane and pentafluoroethane, which comprises (A) reacting 1,1,1-trifluoro-2-chloroethane, hydrogen fluoride and chlorine in a first reactor in the presence of flurorination catalyst at a temperature in the range of from 300° C. to 450° C.; (B) transfering the products of step (A) together with trichloroethylene to a second reactor and reacting them at a temperature in the range of from 200° C. to 400° C.; (C) separating 1,1,1,2-tetrafluoroethane and pentafluoroethane from the resultant products; and (D) feeding the remaining products from step (C) back to the first reactor, wherein the molar ratio of chlorine/1,1,1-trifluoro-2-chloroethanethe in step (A) is in the range of from 0.001 to 0.05

2 Claims, No Drawings

METHOD FOR CONCURRENTLY PRODUCING 1,1,1,2-TETRAFLUOROETHANE AND PENTAFLUOROETHANE

BACKGROUND OF THE INVENTION

1. Field of the Invention

The present invention relates, in general, to a method for producing concurrently different hydrofluorocarbons, more particularly, to a method for producing concurrently 1,1,1,2-tetrafluoroethane (hereinafter, "HFC-134a") and pentafluoroethane (hereinafter, "HFC-125").

2. Description of the Prior Art

Chlorofluorocarbon (hereinafter referred to as "CFC") compounds, extensively used for many purposes such as foaming agents, cleaning agents, aerosol spraying agents and refrigerants, are destined to be prohibited from production and use because they were proven to be a main factor destroying the ozone layer of the stratosphere. Accordingly, intensive research and study have been directed to the development of substitutes which are not harmful to the ozone layer and which are functionally equal to CFCs. As a result of extensive tests for toxicity, stability and physicochemical performance, hydrofluorocarbon (HFC) compounds such as difluoromethane (HFC-32), trifluoromethane (HFC-23), 1,1-difluoromethane (HFC-152a), 1,1,1,2-tetrafluoroethane (HFC-134a) and pentafluoroethane (HFC-125) were revealed to be potent substitutes for CFCs. Among them, HFC-134a turned out to be able to replace a broadly used refrigerant, dichlorodifluoromethane (CFC-12) and thus, it is already in commercial production. In the case of HFC-125, it is being developed for use as a refrigerant at a much lower temperature because it has much lower boiling point of −48.5° C. than −26.5° C. for HFC-134a.

Construction of a plant for producing a hydrofluorocarbon compound is very expensive and it is difficult to predict the supply/demand situation for any given hydrofluorocarbon. There is, thus demand for developing an efficient method for producing various hydrofluorocarbon compounds.

Meanwhile, during production of hydrofluorocarbon compounds, not only the intended hydrofluorocarbon compounds are produced, but by-products such as other hydrofluorocarbon compounds, unreacted starting materials, etc., which make the purification process time-consuming and expensive are also produced. In addition, the catalyst used in the fluorination reaction is gradually deactivated, and thus the reaction efficiency becomes lower.

Various methods has been suggested to produce HFC compounds. U.S. Pat. No. 5,258,561 discloses a method for producing chlorotetrafluoroethane (hereinafter, "HCFC-124") and HFC-125 by reacting HFC-134a, hydrogen fluoride and chlorine in the presence of chromium oxide prepared by the pyrolysis of $(NH_4)_2Cr_2O_7$. However, the molar ratio of chlorine/HFC-134a in this method is relatively high at about 0.7–11, which results in a large amount of by-products including CFC compounds.

PCT International patent application WO 94/11327 discloses a method for co-production of HCFC-124 and HFC-125 by reacting trichloroethylene, HCFC-133a, hydrogen fluoride and chlorine in the presence of a chromium oxide catalyst. In this method, the molar ration of chlorine/HCFC-133a is also high at about 0.5:1–50:1.

PCT International patent application WO 93/25505 discloses a method for co-production of various hydrofluoroalkanes, for example HFC-134a and HFC-125, using a two-step reaction by supplying chlorine to the step of producing HFC-134a from alkanes and hydrogen fluoride. However, in this method in which the molar ratio of chlorine to trichloroethylene is about 1:1 to about 0.05:1, the yield of HFC-134a and HFC-125 are quite low.

SUMMARY OF THE INVENTION

Accordingly, it is a principal object of the present invention to provide a method for producing HFC-134a and HFC-125 concurrently in the same reaction system while restraining production of other hydrofluorocarbons (HFCs) or chlorofluorocarbons (CFCs).

Another object of the present invention is to provide a concurrent production method of HFC-134a and HFC-125, capable of controlling their relative production rates.

The above objects of the present invention may be accomplished by providing a method for producing HFC-134a and HFC-125 in which the supplied amount of chlorine in relation to the amount of HCFC-133a is limited to 5% or less.

The method according to the present invention diminishes the production of other HFC compounds as well as CFC compounds and alleviates deactivation of the catalyt.

DETAILED DESCRIPTION OF THE INVENTION

The present invention comprises (A) reacting 1,1,1-trifluoro-2-chloroethane, hydrogen fluoride and chlorine in a first reactor, in the presence of a flurorination catalyst, at a temperature in the range of 300° C. to 450° C.; (B) transferring the products of step (A) together with trichloroethylene to a second reactor and reacting them at a temperature in the range of 200° C. to 400° C.; (C) separating 1,1,1,2-tetrafluoroethane and pentafluoroethane from the obtained products; and (D) feeding the remaining products from step (C) back to the first reactor wherein the molar ratio of chlorine/1,1,1-trifluoro-2-chloroethanethe in step (A) is from 0.001 to 0.05.

In the first step wherein HCFC-133a, hydrogen fluoride and chlorine are concurrently supplied, HFC-134a ($CF_3CH_2Cl$) and HCFC-123($CF_3CHCl_2$) are produced by the following reactions (1) and (2). Part of the HFC-134a and most of the HCFC-123 react with chlorine and hydrogen fluoride by the reactions (3) and (4), respectively, to produce HCFC-124($CF_3CHClF$) which reacts with hydrogen fluoride to produce HFC-125 through the reaction (5).

The produced mixture from the first reactor is transferred to the second reactor together with trichloroethylene. In the second reactor, HCFC-133a is produced by the following reaction (6).

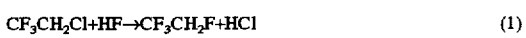 (1)

 (2)

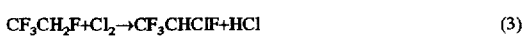 (3)

 (4)

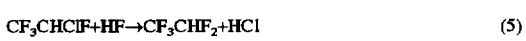 (5)

 (6)

In the method according to the present invention, the reaction temperature at the first reactor ranges from 300° C. to 450° C., and is preferably from 320° C. to 380° C. Below 300° C., the reaction rarely proceeds. Above 450° C., production of by-products and deactivation of the catalyst are accelerated. The contact time generally will be about 1–60 seconds, and is preferably 5–20 seconds, although it depends upon the reaction temperature. The molar ratio of HF/HCFC-133a ranges from about 1 to 30, and is preferably from 6 to 10. When the molar ratio is more than 10, productivity is decreased and thus it is disadvantageous from an economic point of view. The molar ratio of Cl/HCFC-133a ranges from 0.001–0.07, and is preferably from 0.01 to 0.05. When the molar ratio is more than 0.05, production of chlorine-containing compounds such as pentafluorochloroethane, etc. which destroy the ozone layer is increased.

The reaction temperature at the second reactor ranges from 200° C. to 400° C., and is preferably from 250° C. to 320° C. The contact time generally will be from about 1–20 seconds depending upon the reaction temperature. The molar ratio of HF/TCE ranges from about 10 to 50, and is preferably from 20 to 40.

In order to efficiently conduct the exothermic reaction at the second reactor, the maximum temperature at the second reactor is restricted by maintaining the temperature of the inlet of the reactor to be lower, or the temperature increase in the reactor is restrained by supplying the reactant materials separately to the several parts of the reactor. For the purpose of maintaining the temperature in the reactor uniformly as well as restraining the production of by-products and deactivation of the catalyst, it is preferable that the temperature in the reactors should be increased slowly.

The catalyst used in the present invention can be any fluorination catalyst known in this technical field. Exemplary catalysts are those containing chromium oxyfluoride and magnesium oxide, optionally in combination with catalytically active metals such as zinc, cobalt, nickel, etc.

In the following examples, two monotube-type reactors interconnected in series were used and attended with accessory equipments including a vaporizer, a preheater and a distillation column. The first reactor was a 5.0 liter Inconel-600(Inco Alloy International) monotube reactor, and the second reactor was a 1.5 liter reactor made of the same material. The reactors were installed inside of a cylindrical electrical furnace equipped with an automatic temperature controller. Reactant materials were provided into the reactors using a metering pump to control the flow rate of the reactant materials.

A preheater was located just before the first reactor, to provide hot gaseous materials to the first reactor, and its temperature was adjusted as the discharge temperature became equal to the set temperature at the inlet of the first reactor. The obtained products from the first reactor was provided to the second reactor after being mixed with fresh liquid reactant material at the vaporizer. The vaporizer was adjusted in such a way that the temperature of the discharge therefrom was equal to that at the inlet of the second reactor.

Herein, the terms "conversion of HCFC-133a", "selectivity for HFC-134a" and "selectivity for HFC-125" are defined as follows:

$$\text{Conversion of HCFC-133a (\%)} = \frac{\text{amount of HCFC-133a reacted}}{\text{amount of HCFC-133a supplied}} \times 100$$

$$\text{Selectivity for HFC-134a (\%)} = \frac{\text{amount of HFC-134a produced}}{\text{amount of HCFC-133a reacted}} \times 100$$

$$\text{Selectivity for HFC-125 (\%)} = \frac{\text{amount of HFC-125a produced}}{\text{amount of HCFC-133a reacted}} \times 100$$

A better understanding of the present method may be obtained from the following examples which are set forth to illustrate, and are not to be construed to limit, the present invention.

EXAMPLE I

HCFC-133a, hydrogen fluoride and chlorine at flow rates of 7.0 g-mol/h, 100 g-mol/h and 0.21 g-mol/h, respectively, were mixed and provided through the preheater to the first reactor charged with a catalyst of 5.0 kg comprising chromium hydroxide and magnesium fluoride in which the molar ratio of chormium to magnesium was 1:6. The temperature was kept at 340° C., and the reaction pressure at 8 atm at the first reactor. The contact time was about 7 seconds in respect to room temperature and 1 atm.

The molar composition of the organic products from the first reactor are given as follows:

| HCFC-133a | 74.0% | HFC-134a | 22.5% |
|---|---|---|---|
| HFC-125 | 1.8% | HCFC-124 | 0.9% |
| HCFC-123 | 0.3% | others | 0.5% |

An analysis of these results revealed that the conversion of HCFC-133a was 26.0% and the selectivities for HFC-134a and HFC-125 were 86.5% and 6.9%, respectively. No compounds of CFD-110 series were detected.

The product mixture discharged from the first reactor was mixed with TCE provided at the flow rates of 5.5 g-mol/h at the evaporator, and then provided to the second reactor which was charged with 1.7 kg of the same catalyst as that charged into the first reactor. The temperature in the second reactor was kept at 240°–300° C.

The molar composition of the final organic products from the second reactor are given as follows:

| HCFC-133a | 84.7% | HFC-134a | 12.5% |
|---|---|---|---|
| HFC-125 | 1.0% | HCFC-124 | 0.5% |
| HCFC-123 | 0.2% | TCE | 0.8% |
| others | 0.3% | | |

From an analysis of these results, the conversion of TCE in the second reactor was calculated as 98.0%.

The conversion of HCFC-133a in the first reactor after 720 hours was 25.5%, which is about 98.2% of the initial conversion.

EXAMPLES II–IX

Reactions were conducted using the same equipments and procedures as used in example 1, except that the reaction conditions were as shown in the following Table 1. The results are shown in Table 2.

TABLE 1

| | first reactor | | | | second reactor | |
|---|---|---|---|---|---|---|
| Exam. No. | temp. (°C.) | HF/ 133a | Cl2/ 133a | contact time(s) | HF/TCE | contact time(s) |
| 2 | 340 | 6.0 | 0.02 | 15 | 30 | 5 |
| 3 | 340 | 10.0 | 0.04 | 10 | 30 | 3 |
| 4 | 340 | 8.0 | 0.05 | 20 | 25 | 7 |
| 5 | 350 | 8.0 | 0.05 | 30 | 25 | 10 |
| 6 | 350 | 10.0 | 0.03 | 20 | 20 | 7 |
| 7 | 350 | 7.0 | 0.01 | 15 | 20 | 5 |
| 8 | 380 | 7.0 | 0.02 | 10 | 40 | 3 |
| 9 | 320 | 7.0 | 0.04 | 5 | 35 | 2 |

TABLE 2

| Exam. No. | conversion of 133a (%) | selectivity for 134a (%) | selectivity for 125 (%) | conversion of TCE (%) |
|---|---|---|---|---|
| 2 | 22.9 | 88.6 | 7.2 | 100.0 |
| 3 | 24.5 | 76.5 | 10.4 | 98.5 |
| 4 | 24.8 | 69.7 | 9.3 | 100.0 |
| 5 | 25.5 | 70.3 | 12.6 | 100.0 |
| 6 | 26.2 | 84.3 | 11.3 | 99.2 |
| 7 | 24.8 | 91.3 | 4.9 | 97.3 |
| 8 | 28.7 | 89.6 | 6.4 | 100.0 |
| 9 | 17.5 | 83.2 | 8.8 | 98.0 |

Comparative Example I

Reaction was conducted using the same equipments and procedures as used in example 1, except that the flow rate of chlorine was changed to 0.49 g-mol/h.

The molar composition of the organic products from the first reactor was given as follows:

| HCFC-133a | 72.8% | HFC-134a | 18.3% |
|---|---|---|---|
| HFC-125 | 3.5% | HCFC-124 | 1.9% |
| HCFC-123 | 0.5% | CFC-113 | 0.5% |
| CFC-114 | 0.8% | CFC-114a | 0.7% |
| CFC-114a | 0.7% | others | 0.2% |

From an analysis of these results, the conversion of HCFC-133a was 27.2% and the selectivity for HFC-134a and HFC-125 were 67.3% and 12.9%, respectively. Many other CFC compounds were detected and the total selectivity of the CFC compounds was about 10.3%.

The product mixture discharged from the first reactor was mixed with TCE provided at the rate of 5.5 g-mol/h at the evaporator, and then provided to the second reactor.

The molar composition of the final organic products from the second reactor was given as follows:

| HCFC-133a | 83.8% | HFC-134a | 10.2% |
|---|---|---|---|
| HFC-125 | 2.0% | HCFC-124 | 1.0% |
| HFC-123 | 0.3% | CFC-113 | 0.3% |
| CFC-114 | 0.5% | CFC-114a | 0.4% |
| CFC-115 | 0.5% | TCE | 0.8% |
| others | 0.2% | | |

The conversion of TCE in the second reactor was calculated as 98.0%.

Comparartive Example II

Reaction was conducted using the same equipments and procedures as used in example 1, except that chlorine was not supplied. The initial conversion of HCFC-133a in the first reactor was 25.2%; after 720 hours, the conversion was decreased 21.8%, which was 86.5% of the initial conversion.

Other features, advantages and embodiments of the invention as disclosed herein will be readily apparent to those exercising ordinary skill after reading the foregoing disclosure. In this regard, while specific embodiments of the invention have been described in considerable detail, variations and modifications of these embodiments can be effected without departing from the spirit and scope of the invention as described and claimed.

What is claimed is:

1. A method for concurrently producing 1,1,1,2-tetrafluoroethane and pentafluoroethane, which comprises (A) reacting 1,1,1-trifluoro-2-chloroethane, hydrogen fluoride and chlorine in a first reactor, in the presence of a fluorination catalyst, at a temperature in the range of from 300° C. to 450° C.;

(B) transferring the products of step (A) together with trichloroethylene to a second reactor and reacting them at a temperature in the range of from 200° C. to 400° C.;

(C) separating 1,1,1,2-tetrafluoroethane and pentafluoroethane from the resultant products; and (D) feeding the remaining products from step (C) back to the first reactor, wherein the molar ratio of $Cl_2$/1,1,1-trifluoro-2-chloroethane in step (A) is in the range of from 0.001 to 0.05.

2. The method according to claim 1, wherein said fluorination catalyst comprises chromium oxyfluoride and magnesium fluoride.

* * * * *